United States Patent [19]

Sharpe et al.

[11] Patent Number: 4,958,638

[45] Date of Patent: Sep. 25, 1990

[54] NON-CONTACT VITAL SIGNS MONITOR

[75] Inventors: Steven M. Sharpe, Atlanta; Joseph Seals, Stone Mountain; Anita H. MacDonald, Tucker; Scott R. Crowgey, Avondale Estates, all of Ga.

[73] Assignee: Georgia Tech Research Corporation, Atlanta, Ga.

[21] Appl. No.: 213,783

[22] Filed: Jun. 30, 1988

[51] Int. Cl.$^5$ ............................ A61B 5/02; A61B 5/08
[52] U.S. Cl. ................................. 128/653 R; 128/671; 128/721
[58] Field of Search ............... 128/653, 716, 721, 670, 128/671, 782

[56] References Cited

U.S. PATENT DOCUMENTS

| | | | |
|---|---|---|---|
| 3,483,860 | 12/1969 | Namerow | 128/653 R |
| 3,951,134 | 4/1976 | Malech | 128/653 R |
| 4,085,740 | 4/1978 | Allen, Jr. | 128/653 R |
| 4,488,559 | 12/1984 | Iskander | 128/653 R |
| 4,638,808 | 1/1987 | Mawhinney | 128/653 R |

Primary Examiner—Kyle L. Howell
Assistant Examiner—K. M. Pfaffle
Attorney, Agent, or Firm—Hurt, Richardson, Garner, Todd & Cadenhead

[57] ABSTRACT

An apparatus for measuring simultaneous physiological parameters such as heart rate and respiration without physically connecting electrodes or other sensors to the body. A beam of frequency modulated continuous wave radio frequency energy is directed towards the body of a subject. The reflected signal contains phase information representing the movement of the surface of the body, from which respiration and heartbeat information can be obtained. The reflected phase modulated energy is received and demodulated by the apparatus using synchronous quadrature detection. The quadrature signals so obtained are then signal processed to obtain the heartbeat and respiratory information of interest.

21 Claims, 6 Drawing Sheets

NON-CONTACT VITAL SIGNS MONITOR

GOVERNMENT INTEREST

This invention was made with Government support under contract No. N 00014-82C-0930 awarded by the Department of the Navy and under Contract No. F 33615-83D-0601 awarded by the Department of the Air Force. The Government has certain rights in the invention.

BACKGROUND OF THE INVENTION

This invention relates in general to the use of radar techniques to detect minute body movements which are associated with cardiac and respiratory activity. The invention is based on the principle that breathing and heartbeat produce measurable phase changes in electromagnetic waves as they reflect off of a living person. The invention offers significant advantages over other similar and earlier approaches, including greater sensitivity, lower radiated power, improved reliability and lower cost.

Functionally, the non-invasive, electromagnetically-based Vital Signs Monitor (VSM) is an extremely sensitive motion detection system capable of detecting small body motions produced by respiratory and cardiac functioning. Motion detection is achieved by transmitting an interrogating electromagnetic field at the target of interest, and then measuring the time-delay of the return signal reflected back from the surface of the target. When the target surface is moving, as does the surface of the chest in conjunction with respiratory and cardiac activities, corresponding variations will be observed in the measured time delay. The observed variations can be used to determine motion-related target parameters such as displacement and velocity.

In the medical field, it is essential that a subject's respiration and heartbeat be capable of being measured. The medical profession is accustomed to voltage-derived electrocardiogram waveforms for monitoring heartbeat. Most respiration monitors also require physical connection to the subject's body. Many commercially-available devices are available for measuring heart and respiration rates, but most of them are electrode-based requiring physical contact with the subject. Devices requiring physical contact, however, are difficult to use on children susceptible to sudden infant death syndrome (SIDS) or burn patients who cannot tolerate the touch of electrodes. Many infants wear sensors while they sleep that trigger an alarm if their breathing stops, but electrodes attached to the child can be jarred loose as the infant tosses and turns.

The invention has similarities with motion-detection systems based on ultrasonic or optical techniques. However, an electromagnetically-based approach offers several advantages for monitoring of vital signs-related motions. For example, with proper antenna design, an interrogating electromagnetic field will suffer minimal attenuation while propagating in air (unlike ultrasonic signals which propagate poorly in air). Thus, the electromagnetically-based Vital Signs Monitor can easily be used in a completely non-contacting mode and can, in fact, be placed an appreciable distance from the test subject if required. Electromagnetic signals in the microwave band are also capable of penetrating through heavy clothing. This offers advantages over optical techniques which would have a difficult time of detecting motion through even thin clothing. Another feature of an electromagnetically-based approach is that the system could be designed to simultaneously interrogate the entire chest surface and provide information pertaining to any respiratory or cardiac function manifested as chest wall motions. Conversely, by modifying the antenna design, a localized region of the chest surface could be interrogated to obtain information about some specific aspect of respiratory or cardiac function. Such versatility would be difficult to achieve with other motion detection techniques.

In the prior art the patent to Allen, U.S. Pat. No. 4,085,740 discloses a method for measuring physiological parameters such as pulse rate and respiration without electrodes or other sensors being connected to the body. A beam of electromagnetic energy is directed at the region of interest which undergoes physical displacement representing variations in the parameter to be measured. The phase of the reflected energy when compared with the transmitted energy indicates the amount of actual physical movement of the body region concerned. The method does disclose simultaneous detection and processing of respiration and heart beat; however, frequency modulation is not used, therefore and the subject must be reasonably still. The receiver includes two channels and in one of them the received signal is mixed with a signal substantially in quadrature with the transmitted signal to maximize amplitude output in those cases in which the received signal is 180° out of phase with the transmitted signal.

The patent to Kaplan, et al., U.S. Pat. No. 3,993,995 discloses an apparatus for monitoring the respiration of a patient without making physical contact. A portion of the patient's body is illuminated by a transmitted probe signal with the reflected echo signal detected by a monitor. The phase difference between the transmitted and reflected signals is determined in a quadrature mixer which generates outputs indicative of the sine and cosine of the difference signal. These two outputs are coupled to differentiators and when both time derivatives are substantially zero an x-ray unit is triggered since it represents an instant of respiration extrema (apnea). The outputs of the quadrature mixer are also coupled to a direction of motion detector which indicates inhalation or exhalation.

The patent to Kearns, U.S. Pat. No. 4,289,142 discloses a respiration monitor and x-ray triggering apparatus in which a carrier signal is injected into the patient's thorax which is indicative of the transthoracic impedance of the patient. This impedance changes as a function of the respiration cycle. The carrier signal is injected through electrodes coupled to the patient's thorax. The transthoracic impedance has an alternating current component having a respiratory component between 0.2 to 5 ohms and a cardiac component varying between 0.02 to 0.2 ohms.

The patent to Robertson et al., U.S. Pat. No. 3,524,058 discloses a respiration monitor which uses body electrodes to direct an electric current to a particular part of the patient's body where changes in electrical impedance provide output signals that vary with respiration.

The patent to Bloice, U.S. Pat. No. 3,796,208 discloses an apparatus for monitoring movements of a patient including a microwave scanner (doppler radar) which creates a movement sensitive field surrounding part of the patient. Movements of the patient create disturbances in the field which are monitored and which trigger alarm circuitry.

Also in the prior art, apexcardiograms (ACG), which represent a contact technique for measuring small chest surface motions overlying the cardiac apex, have been used to estimate cardiac contractility, left ventricular end-diastolic pressure, pressure changes during atrial systole and cardiac ejection fraction, in addition to diagnosing myocardial wall abnormalities and dysfunction. One of the problems associated with the use of an ACG for the estimation of cardiac function is that the motions recorded are indicative only of activity at the apex of the heart and not of the heart as a whole. Analysis of the VSM waveform is potentially a better choice for estimation of cardiac function since the larger beamwidth of the VSM antenna actually integrates motion over a certain area of the chest. In addition, since the VSM waveform appears to contain information related to aortic and other vascular pulses, it can be used to measure pulse transit times directly out of the heart into the aorta. This measurement can potentially be used as a non-invasive, non-contact means of estimating blood pressure as discussed by L. A. Geddes, M. Voelz, C. F. Babbs, J. D. Bourland and W. A. Tucker in "Pulse Transit Time as Indicator of Arterial Blood Pressure," *Psychophysiology*, Vol. 18, No. 1, pp. 71-74, 1981. This paper showed that the pulse-wave velocity in the dog aorta increased linearly with increasing diastolic pressure. Similarly, pulse pressures may be related to either the magnitude of the aortic peak in the VSM waveform, or possibly to the rate of rise of this peak.

SUMMARY OF THE PRESENT INVENTION

It is therefore an object of the present invention to Provide an electromagnetic vital signs monitor that can reliably measure simultaneously both heart and respiration rates.

It is a further object of this invention to provide a device for measuring physiological parameters without physically contacting the subject with sensors or like attachments.

It is a further object of this invention to provide a device for measuring physiological parameters of subjects remotely at distances up to approximately 20 feet.

It is a further object of this invention to provide a device for non-contact and non-invasive diagnosis and monitoring capabilities of cardiac, pulmonary, and thoracic mechanical functions resulting from normal or induced physiological responses, trauma, disease or response to therapy.

It is a further object of this invention to provide a device for measuring remotely the physiological parameters of subjects that are fully clothed and that can be either stationary or moving while sitting or standing.

It is a still further object of this invention to provide a device which can be used as an apnea monitor for patients in hospital or clinic intensive care units, or as a patient monitor in burn or trauma clinics or in nursing homes.

It is a still further object of this invention to provide a portable device that can be taken into patient areas for the purpose of measuring heart beat and respiration rates.

It is a still further object of this invention to detect the presence of persons in visually obstructed areas or under debris resulting from certain disasters.

The non-contact electromagnetic vital signs monitor is comprised of a coherent, linear, frequency modulated continuous wave radar with refinements to optimize the detection of small body movements. The transmitter of the device is frequency modulated by a linear ramp derived from a master clock. The transmitted signal is fed to the radio frequency (RF) network which routes a portion of the energy to the antenna which then interrogates the subject. Signals reflected by the subject containing motion-related phase modulation are intercepted by the antenna and applied to the RF network where they are mixed with a portion of the original signal.

The mixing process produces a difference signal which contains harmonics of the original modulating ramp. Each harmonic line is surrounded by sidebands which are related to the body movements. The relative levels of these sidebands are a function of target range, transmitter frequency deviation, and harmonic number. By properly choosing these latter two parameters, signals from a desired range can be detected while others are suppressed. The process is further refined to result in more ideal range discrimination by multiplication by a weighting function synchronized to the ramp which reduces the range sidelobes.

The final synchronous demodulation is accomplished by mixing the received signal (after weighting) with both the in-phase and quadrature components of the desired harmonic of the modulating ramp which is generated by a synthesizer. After recovery of the in-phase and quadrature components of the received signal, sophisticated digital signal processing can be economically applied since the bandwidths are relatively low. In the preferred embodiment, a high order linear phase finite impulse response digital filter is used on each channel to reduce the dominance of the strong respiratory signal. A complex autocorrelation is performed from which the rates of interest may be calculated.

Still other objects, features and attendant advantages of the present invention will become apparent to those skilled in the art from a reading of the following detailed description of the preferred embodiment, taken in conjunction with the accompanying drawings.

DETAILED DESCRIPTION OF THE INVENTION

The apparatus which is used to carry out the method of the present invention is referred to hereinafter as the VITAL SIGNS MONITOR (VSM).

At the electromagnetic frequencies of 3 and 10 GHz that have been used in the VSM, the surface of the body is highly reflective to incident electromagnetic fields. In addition, biological tissue is very lossy at these frequencies and there is minimal penetration of radiated electromagnetic energy into the body. Therefore, a return signal from a radiated electromagnetic field incident on the body will primarily contain information associated with events occurring at the body surface.

Motion of a target with an electromagnetically-reflective surface can be detected by transmitting an interrogating signal at the target surface, and then measuring the motion related time-delay of the return signal that reflects back from the target. The interrogating signal travels at the speed of light and the time delay experienced by the return signal is equal to the round-trip distance to the target surface, divided by the speed of light. Thus, the time delay of the return signal is proportional to the range or distance to the target surface. If the target is moving in a manner that varies the target range, variations in the measured time delay can be used as a measure of target motion.

A simple mathematical model can be used to describe this motion detection phenomenon. Assume that a sinusoidal interrogating signal, vi(t), of the following form is transmitted at the target of interest, $$vi(t) = A \sin(wt). \quad (1)$$

The return signal, vr(t), reflected from the target surface can be represented as, $$vr(t) = kA \sin w(t+T). \quad (2)$$

The parameter k represents losses due to propagation attenuation and imperfect reflection from the target surface. The parameter T represents the time delay information of interest. To extract this information, a portion of the transmitted signal vi(t) can be used as a reference signal to demodulate the return signal vr(t). By combining vi(t) and vr(t) and passing them through a nonlinear device such as a mixer or square-law detector, an output signal vo(t) of the following form can be produced, $$vo(t) = \tfrac{1}{2} k \cos(wT). \quad (3)$$

The parameter k' includes the previously defined parameter k as well as conversion losses associated with devices (splitters, couplers, mixers, etc.) involved in the demodulation process.

Assuming that k' is relatively constant for small target motions, the motion-related information is contained within the argument (i.e., wT) of the cosine function. R(t) is defined as the range to the target surface (the range is time-varying because of the target motion). As previously noted, T is then equal to 2R(t)/c, where c is the speed of light. Using this relationship and noting that 2 pi c/w equals the wavelength (denoted as L), Equation (3) can be expressed in the form, $$vo(t) = \tfrac{1}{2} k' \cos(4 \text{ pi } R(t)/L). \quad (4)$$

This result provides insight into the operation and potential problems of electromagnetically-based motion detection. One useful observation is that only the cosine of the angular (phase) information of interest is accessible. Thus, for accurate recovery of the desired motion information (i.e., R(t)), both the nominal distance to the target and the magnitude of the target motion must fulfill certain requirements. The nominal target distance should be set to insure that the average value of the phase term in Equation (4) is an odd integer multiple of one-half wavelength. This is equivalent to requiring that vi(t) and vr(t) be in phase.

The motion magnitude should also be small enough to insure that the motion-related variations in the phase term do not exceed approximately ±45°. This limits operation to portions of the cosine function that approximate a straight line and insures that Equation (4) produces a nearly linear approximation of the motion R(t). This requirement is fulfilled if the target motion is small in comparison to the wavelength of the interrogating electromagnetic field. From Equation (4), it can be deduced that the magnitude of the target motion should not exceed approximately ± one-eighth wavelength. The requirements posed by Equation (4) result from the fact that detection systems based on the preceding model are not true coherent systems capable of providing both phase and amplitude information. This problem can be eliminated by splitting vr(t) into two signals. One of these signals is demodulated against vi(t) to produce the result obtained in Equation (4). The second signal is demodulated against a signal in phase quadrature with vi(t) to produce a result of the form $\tfrac{1}{2}k'\sin(wT)$. From trigonometric relationships, the sine and cosine terms can then be used to directly determine the desired phase information.

The use of quadrature channels eliminates the previously discussed limitations on the target motion R(t) and development of such a capability has been a focal point of this invention.

Figure 1:
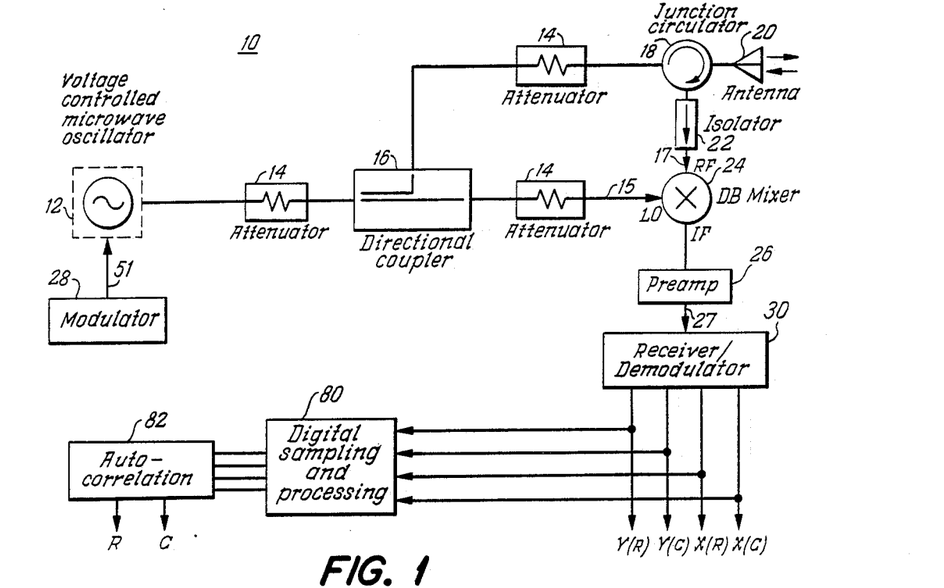
FIG. 1 is a block diagram of the VSM.

Turning now to the figures in which like numerals denote like parts, a specific embodiment of the basic design for the VSM is shown in FIG. 1. Although there are no specific operating frequency limitations on the VSM, systems operating at frequencies of 3 GHz and 10 GHz have been implemented so far. Thus for these specific implementations each RF section of VSM 10 includes: (1) a voltage controllable microwave oscillator 12 to produce a frequency modulated RF signal, (2) a directional coupler 16 to split the voltage controlled microwave oscillators output, (3) fixed attenuators 14 to control the radiated power and local oscillator level 15, (4) an antenna 20 for transmitting the interrogating field and receiving the target return signal, (5) a circulator 18 to recover the return signal from the antenna, (6) a double balanced mixer 24 for demodulating the RF return signal to obtain an IF signal (the receiver/demodulator performs another demodulation to retrieve the phase information from the IF signal); (7) an isolator 22 to prevent local oscillator (LO) level 5 to RF 17 leakage through the double balanced mixer 24 from reaching the antenna 20 and (8) a preamplifier 26 to minimize noise problems. In addition, a coaxial low-pass filter is placed on the mixer IF in the 3 GHz system to block LO to IF leakage. Other configurations of hardware components can be used to mix the transmitted and return signals to produce the IF result; however, the embodiment described here is the best mode currently known to the inventors.

Frequency modulating the voltage controlled microwave oscillator 12 is an effective and convenient way to reduce the effects of low frequency semiconductor noise. With frequency modulation, the motion-related information of interest that is output by the double balanced mixer 24 appears as sidebands centered at the modulating frequency. By using a modulating frequency of several kHz, the largest portion of the low-frequency flicker noise is avoided and greater receiver sensitivity is achieved.

The modulator 28 provides a time-varying waveform that can be used to frequency modulate the voltage controlled microwave oscillator 12 in the RF section of the VSM. The main advantage of frequency modulating the voltage controlled microwave oscillator 12 is that it makes it possible to achieve greater receiver sensitivity, which in turn, enables the use of lower and thus safer, radiated power levels.

Figure 2:
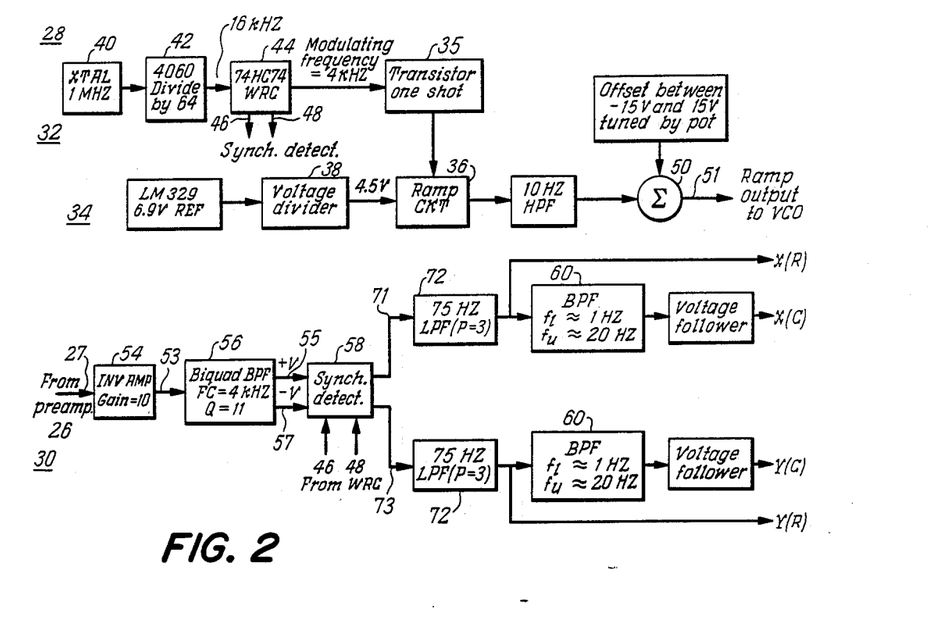
FIG. 2 is a functional diagram of the modulator-receiver/demodulator without a weighting circuit.
Figure 3:
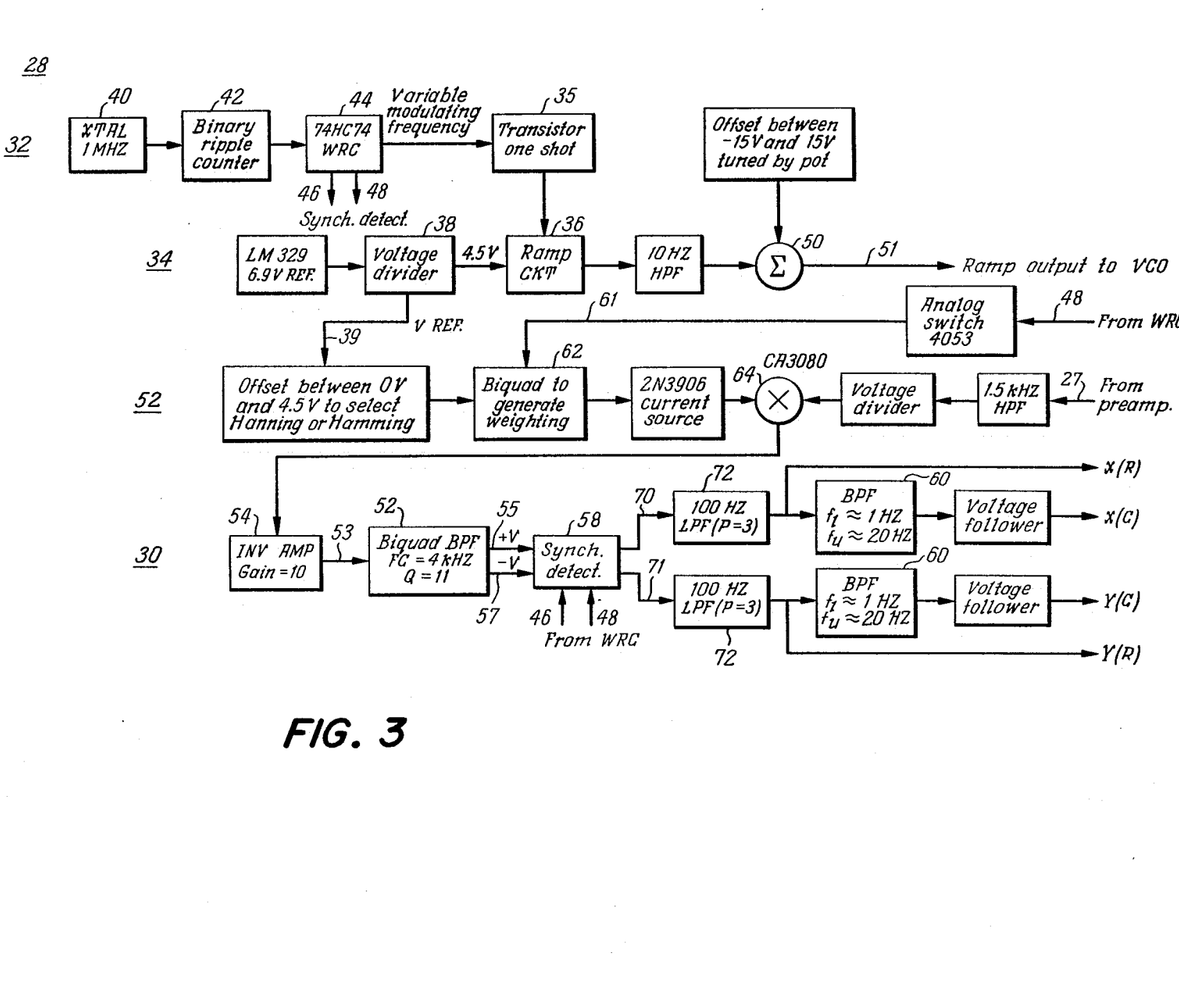
FIG. 3 is a functional diagram of the modulator-receiver/demodulator with a weighting circuit.

The modulator 28 can be conveniently divided into two sections: a digital section 32 which is used to provide all timing information, and an analog section 34 which is used to form the actual ramp waveform used as the modulating signal. A functional diagram is shown in FIGS. 2 and 3. An operational amplifier-based Howland integrator in ramp circuit 36 is used to create the basic ramp waveform from inputs from a oneshot 55 and a voltage divider 38. This particular integrator is used to provide a simple means of generating a nonlinear ramp to compensate for the nonlinear tuning curve of the voltage controlled microwave oscillator 12, thereby producing a relatively linear frequency ramp. Alternative ramp generator circuits could be used as well. A transistor in ramp circuit 36 controls the charging of the integrator. When the input to the transistor is zero volts, the transistor cuts off and a capacitor in ramp circuit 36 charges to 4.5 V (the reference voltage which is the output 39 of the voltage divider 38). The current that charges the capacitor consists of two parts: a constant current produced by the reference input voltage and input resistor, and a variable current which is the ratio of the voltage being amplified by the operational amplifier and a resistance R which is a function of both the input resistor and a variable resistor. The variable resistor is adjusted so that R may be either positive or negative. The result is that the ramp may be expressed in the form $$V(t) = V_0(1 - \exp(-t/RC)) \quad (5)$$

where $V_0$ is a constant. When R is positive, the ramp bows upward; and when R is negative the ramp bows downward. A high input (+5 V) to the transistor saturates the transistor and rapidly discharged the capacitor, resetting the ramp.

The combination of the transistor and the Howland integrator in this particular embodiment produces a basic modulating ramp waveform. However, additional circuitry controls the amplitude and offset level of the modulating waveform and compensates for nonlinearities of the voltage controlled microwave oscillator 12. The ramp amplitude controls the total frequency range over which the voltage controlled microwave oscillator 12 is modulated. The offset level controls the center frequency. At the output of the Howland integrator, a potentiometer acting as a voltage divider controls the amplitude of the ramp. The offset level of the ramp waveform is controlled by a summing network 50 that can be used to add or subtract a DC level to the output of the integrator as can be seen in FIG. 2. The ability to control the ramp amplitude and offset level is important to insure that the modulating frequency is centered at an appropriate value and to insure that operation is performed over a suitable linear portion of the voltage controlled microwave oscillator's 12 tuning response.

The digital timing circuit 32 generates the signal required to control charging and discharging of the integrator as can be seen in FIG. 2. In the preferred embodiment, a 1 MHz crystal oscillator 40 is used as a stable timing reference. The output of this crystal oscillator 40 is input to a binary ripple counter 42 that divides the 1 MHz crystal frequency by a factor of $2^n$, where n is an integer between 6 and 9. The resultant signal from the ripple counter 42 is then fed into a two-stage walking ring counter 44 where two significant operations occur. The walking ring counter 44 provides an additional division of four in frequency. The output of the walking ring counter 44 is at the modulating frequency, which is one of the following: 4 kHz, 2 kHz, 1 kHz, or 500 Hz. In addition, the walking ring counter 44 outputs two periodic square waves on lines 46, 48 that are exactly in phase quadrature (relative phase difference of 90°). These quadrature signals are essential to the synchronous detectors 58 in the receiver/demodulator 30 which provide the VSM 10 with a quadrature channel capability.

The VSM 10 employs a receiver consisting of a front-end double-balanced mixer 24 and a receiver/demodulator that serves as a narrow band detector by demodulating the IF signal to obtain the phase information; this is the second demodulation performed in the VSM. With the FM-CW approach used in the VSM 10, motion-related information output from the mixer appears as sidebands centered around a carrier frequency of 4 kHz. The carrier frequency is an integral multiple of the modulating frequency. An appropriate narrow band detection scheme is required to extract these motion-related sidebands.

The receiver/demodulator 30 represents the required detection scheme and consists of a low noise preamplifier 26 that provides needed gain and filtering at the carrier frequency, an optional weighting circuit 52 to attenuate extraneous returns, an inverting amplifier 54, a band pass filter 56 to remove unwanted frequency components (especially third order harmonics) prior to synchronous detection, a pair of synchronous detectors, shown within block 58, that enable coherent detection of both amplitude and phase information, and a pair of band pass filters 60 to remove unwanted frequency components in the outputs of the synchronous detectors (DC components and high frequency mixing products). A block diagram of the receiver/demodulator 30 is contained in the lower half of the VSM block diagrams in FIGS. 2 and 3.

Use of the weighting circuit 52 improves the ability of the ramp-based frequency modulation technique used in the VSM 10 to reject extraneous return signals. With this frequency modulation technique, the demodulation output of the VSM 10 contains sinusoidal bursts due to returns from the subject being evaluated. These sinusoidal bursts repeat at a rate equal to the modulating frequency and the frequency of these bursts is a function of the subject's distance from the VSM 10 (range). However, discontinuities exist at end points of each sinusoidal burst due to recycling of the modulating ramp. These discontinuities cause the demodulated return signal to have a spectrum containing harmonics of the modulating frequency. The undesired harmonic components, also know as range sidelobes, enable return signals from other subjects to generate frequency components at the receiver frequency.

Weighting functions substantially reduce the effects of these discontinuities. To achieve range sidelobe suppression in this manner, a demodulated return signal is multiplied by a weighting function which is synchronized with a sinusoidal burst in the demodulated return signal. Weighting functions are usually bell-shaped and have a value of unity at their center with ends that taper to a small value. The resulting product of a demodulator return signal in the selected window still contains discontinuities, but the weighting procedure reduces their significance and results in a more ideal spectrum.

Figure 4:
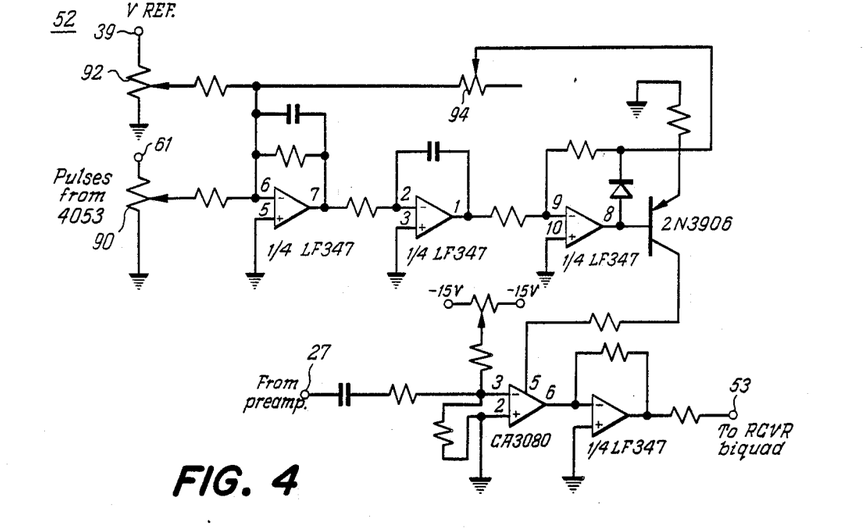
FIG. 4 is a schematic diagram of the weighting circuit.

The VSM 10 may be configured with or without weighting. As shown in FIG. 2, when weighting is not used, the ramp frequency equals the, receiver frequency, 4 kHz. FIG. 3 shows that, when weighting is used, the ramp frequency equals 500 Hz, 1 kHz or 2 kHz. The weighting circuit 52 is shown in FIG. 4. The weighting circuit 52 has been designed so that the detected signal 27 from the preamplifier 26 may be multiplied by one of two weighting functions, the Hamming window or the Hanning window. Other windows could be chosen and the two that have been implemented are not a limitation of the VSM 10. The equations for each of the windows are given below:

Hanning:

$$w(t) = 0.50 - 0.50 \cos(2 \pi t), 0 < t < 1 \quad (6)$$

Hamming:
$$w(t) = 0.54 - 0.46 \cos(2 \pi t), 0 < t < 1 \quad (7)$$

Pulses at the modulating frequency are input into the operational amplifier-based bi-quad low pass filter 62. Alternatively, many other low pass filter designs can be implemented to achieve the same result. The low pass filter 62 attenuates the higher ordered harmonics of the pulses, generating a sinusoidal signal. The potentiometer 90 at the input varies the input signal level so that the amplitude of the sinusoidal term in the weighting function can be varied depending on the choice of weighting function. A summing junction 91 allows a DC offset determined by another potentiometer 92 to be added to the sinusoidal term and generates the desired weighting function. The remaining potentiometer 92 involved with the generation of the weighting function sets the cutoff frequency of the low-pass bi-quad bandpass filter 56 precisely. The transistor acts as a voltage-to-current converter, supplying a current proportional to the weighting function to the CA3080 transconductance amplifier 64. The CA3080 64 essentially multiplies the weighting function by the signal output 27 from the preamplifier. The output of the weighting circuit 52 is then input to the receiver 30.

The bi-quad bandpass filter 56 provides additional rejection of DC and low frequency components and also suppresses any harmonics of the modulating frequency that are generated by the double-balanced mixer 24. The bi-quad design permits the cutoff frequency of the filter 56 to be tuned by adjustment of a single feedback transistor and has the unique characteristic of maintaining a constant absolute bandwidth as it is tuned. The inverting amplifier stage used in the bi-quad bandpass filter 56 Provides two signals identical in amplitude but opposite in phase. These signals each have a frequency of 4 kHz and contain low frequency side bands corresponding to the motion-related information of interest. The availability of the out-of-phase signals enable synchronous detection using a conveniently implemented chopper approach.

Figure 5:
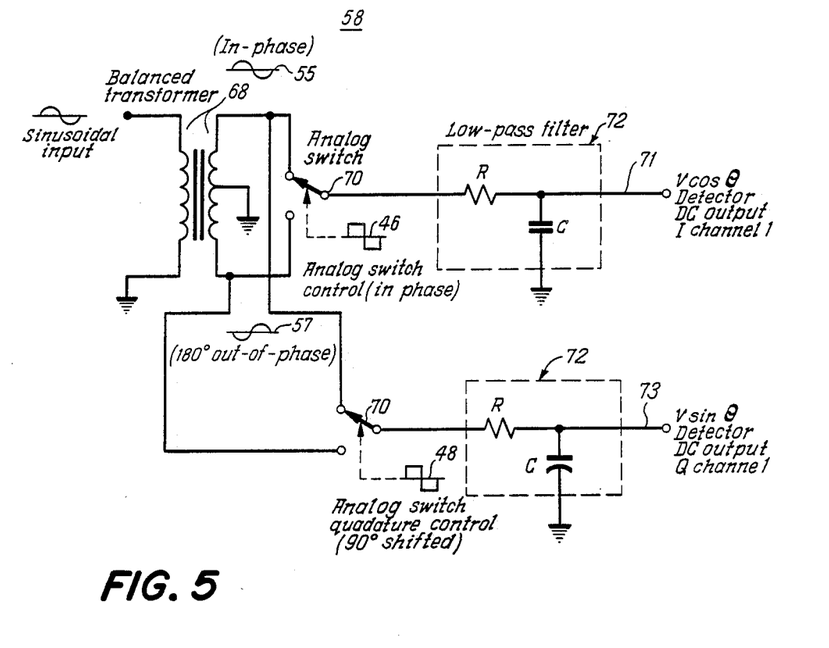
FIG. 5 is a schematic diagram of the chopper-based synchronous detectors used in a demodulator.

A model of a chopper-based detector 58 is shown in FIG. 5. Because of its out of phase outputs, the bi-quad bandpass filter 56 is represented as a center tapped transformer 68. The chopper (electronic switch) 70 is switched between the two outputs of the transformer 68 at a frequency of 4 kHz. Since the chopper frequency is identical to that of the information from the transformer 68, the sum and difference frequency terms outputted by the chopper 70 contain a DC term (difference frequency component) and a 8 kHz term (sum frequency component). The low pass filter 72 following the chopper is used to remove the undesired sum frequency component. The remaining DC term is dependent on the phase difference between the information signal (55 or 57) into the transformer 68 and the reference signal (46 or 48) controlling switching of the chopper.

For the demodulator 30 in the VSM 10, a synchronous detector 58 is employed. A model of the detector 58 is synchronous to the model shown in, FIG. 5. The reference signals 46 and 48 into the synchronous detector 58 have a phase difference of 90° (the quadrature-phase reference signals are provided by the walking ring counter 44 in the, modulator subsystem). Thus, the one of the outputs 71 from the synchronous detector 58 can be considered an in-phase or I channel term that is equivalent to the cosine of the phase of the information signal. The other output 73, from the synchronous detector 58 can be considered a quadrature or Q channel term equivalent to the, sine of the information signal. The I and Q signals, 71 and 73, can be evaluated jointly or independently to extract the motion-related information of interest.

The phase of the demodulated return signal varies as a function of target motion. Therefore, the I and Q signals, 71 and 73, that are output by the synchronous detector 58 are not true DC terms. Instead, these signals occupy a frequency band related to that of the motion being detected. Since the VSM 10 was designed to provide an almost linear estimate of target motion, the frequency band of the I and Q channels is the same as that of the respiratory and cardiac motions, being, detected. Thus, filters 60 used on the outputs, 71 and 73 of the synchronous detector must have sufficient bandwidth to pass information in the respiratory and cardiac bands but must be narrow enough to reject unwanted noise and mixing products.

Lowpass filters 72 and bandpass filters 60 with passbands of approximately 0.1–75 Hz are used to filter the outputs 71 and 73 of the synchronous detector 58. The 0.1 Hz lower frequency cutoff of filter 60 effectively blocks DC terms but is low enough to pass slow respiratory information. The 75 Hz low-pass cutoff frequency filter 72 blocks the 8 kHz sum frequency term generated by the synchronous detectors 58 but is high enough to pass fast cardiac motion. In addition, the 75 Hz cutoff should make it possible to determine if vibrations associated with respiratory and cardiac sounds can be detected. Cascaded together, the filters 72, 60 have such a wide passband that for all practical purposes, the data output may be considered unprocessed. Therefore, suitable signal processing techniques must be used to extract useful information from the output data.

In order to digitally process the output data, the I and Q channels are sampled at a rate of 100 Hz by a sampler included in the Digital Sampling and Processing block 80, shown in FIG. 1. Prior to sampling, the I and Q channels are input to a pair of 34 Hz second order low pass anti-aliasing filters, which are included in digital sampling block 80 in FIG. 1. Without these anti-aliasing filters, it would be possible for signal components over 50 Hz, half the sampling rate, to take on the identity of lower frequencies, resulting in signal distortion.

Typically, respiratory rates of normal subjects correspond to frequencies of approximately 0.12–0.30 Hz (7–18 breaths per minute) while cardiac rates correspond to approximately 0.8–1.5 Hz (48–90 beats per minute). Since there is more than an octave difference between the highest respiratory frequency and the lowest cardiac frequency, it is possible to examine the individual respiratory and cardiac components.

Figure 6A:
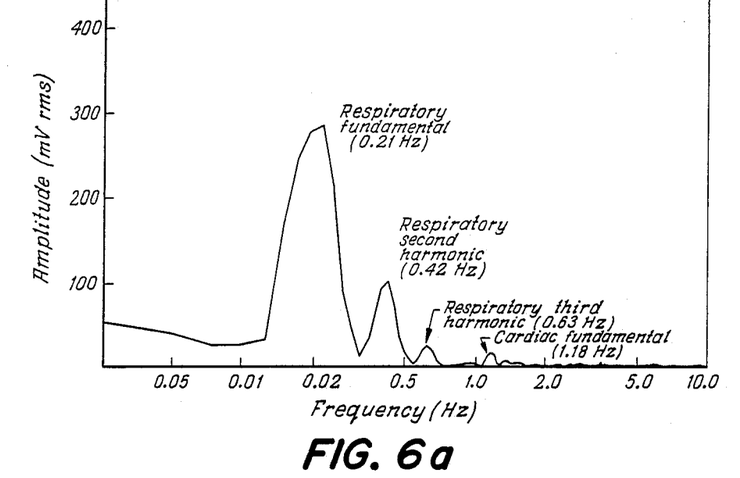
FIG. 6A is a power spectrum for a composite VSM output displaying respiratory and cardiac spectral components.
Figure 6B:
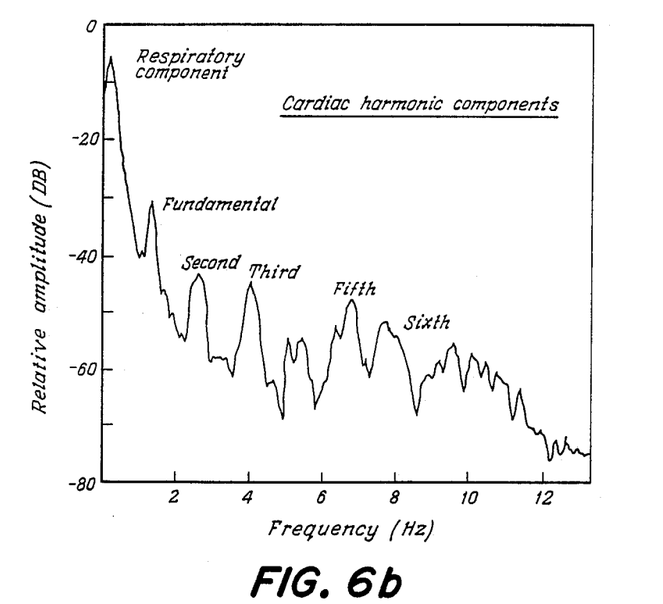
FIG. 6B is a power spectrum for a composite VSM output using logarithmic amplitude and linear frequency scale to demonstrate harmonic structure of cardiac information.

FIG. 6A shows a power spectrum for a composite VSM return signal obtained with a laboratory signal analyzer. The linear amplitude and logarithmic frequency scales permit detailed evaluation of the respiratory spectrum. The fundamental respiratory component has an RMS amplitude of 280 millivolts while the fundamental cardiac component has an RMS amplitude of only 17.9 millivolts. The respiratory component occurs at 0.21 Hz corresponding to a respiratory rate of approximately 12 to 13 breaths per minute. The smaller cardiac spectral component occurs at 1.18 Hz corresponding to the subject's heart rate of approximately 70–71 beats per minute. Harmonics of the respiratory fundamental can also be observed at 0.42 and 0.63 Hz. The second harmonic of the respiratory motion is approximately 9 dB lower than the fundamental respiratory component. The third harmonic is approximately 21 dB below the fundamental respiratory component. Knowledge of the relative strengths of the individual harmonic components can be used to identify specific features in the corresponding time based signal. Such information can be useful for characterizing or classifying the breathing pattern. By changing to a more convenient logarithmic amplitude scale and a linear frequency scale, it is possible to better evaluate the cardiac spectrum as shown in FIG. 6B. In this figure, wider frequency resolution has resulted in a smearing of the respiratory portion of the spectrum so that only a single respiratory component appears at a frequency of approximately 0.15 Hz. It can be seen that the fundamental, second, third, fifth and possibly sixth harmonics are strong while the fourth harmonic is partially suppressed. Again, knowledge of such spectral information is valuable for evaluating aspects of cardiac function. One of the difficulties with spectral analysis is that the rates determined actually represent the average rate of several events. With average but not instantaneous rate values available, it is difficult to compute useful parameters such as heart rate variability.

If cardiac and respiratory functions are to be evaluated from familiar time-based waveforms, filtering techniques capable of separating the composite signal from the VSM 10 into its individual respiratory and cardiac components are required. In practice, it is relatively simple to build filters to extract the desired respiratory component while several factors combine to make recovery of cardiac information difficult to achieve. For example, for most test subjects the peak-to-peak levels of the respiratory-related signal is a factor of 5–20 times greater than that of the corresponding cardiac-related signal. Thus, filters used to recover cardiac information in the presence of a strong respiratory signal must greatly attenuate the low-frequency band occupied by the respiratory information. This requires filters with a sharp-rolloff (i.e., a large number of poles). Because of the potentially small separation between the respiratory and cardiac information bands, it is necessary that a filter used to recover cardiac information have a precise cutoff frequency. In addition, since respiratory and cardiac rates will vary significantly, it is necessary that the filter's cutoff frequency be adaptive or at least adjustable. The limited capabilities of simple analog filters appear inadequate for this task. Thus, a digital signal processing capability is required for the VSM to achieve reliable rate determination and to produce diagnostically useful respiratory and cardiac waveforms. What follows is a description of the signal processing methods used in the VSM, but those skilled in the art will understand alternative implementations are possible.

In order to determine the cardiac rates, the analog I and Q signals are first sampled at a 100 Hz rate and then high pass filtered digitally with a cutoff frequency between 0.75 and 1.0 Hz. These filters, though not shown individually, are included with the Digital Sampling and Processing block of FIG. 1. The complex autocorrelation to the two filtered signals is then computed, as shown in FIG. 1 by the Autocorrelation block 82. Periodicities in the signal due to cardiac related motions appear as relative maxima in the real part of the autocorrelation function. The signal processing is not performed in real time.

Figure 7A:
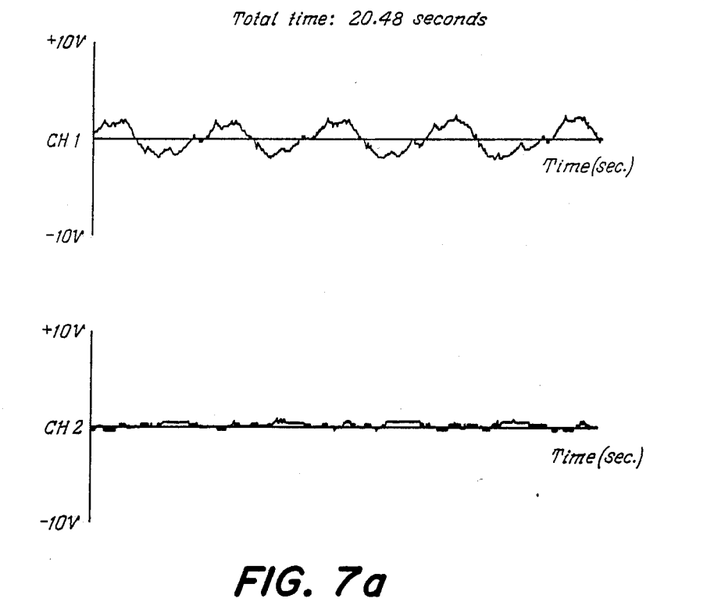
FIG. 7A is a VSM return signal from a stationary subject immediately after sampling.
Figure 7B:
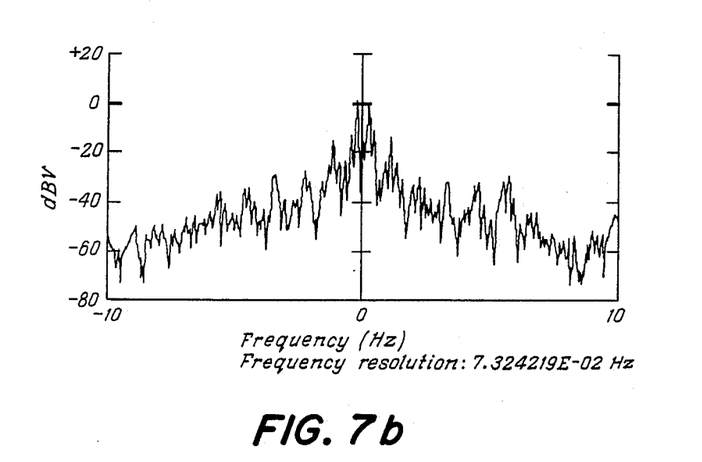
FIG. 7B is a result of applying a Fast Fourier Transform to the sampled data.
Figure 7C:
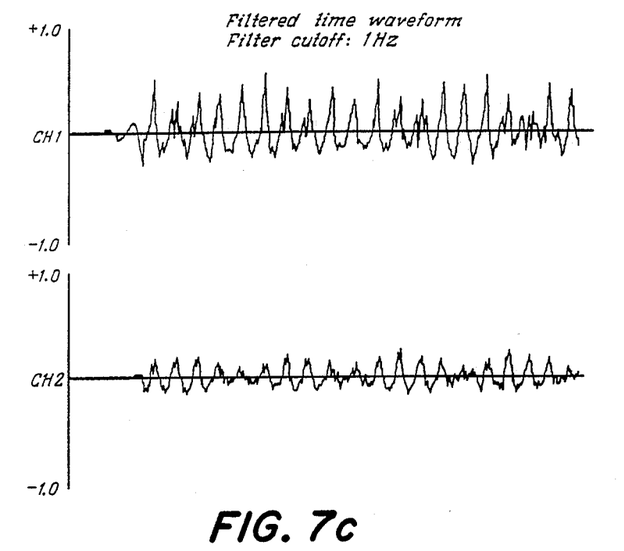
FIG. 7C is a result of applying a digital high pass filter to the VSM return signal.
Figure 7D:
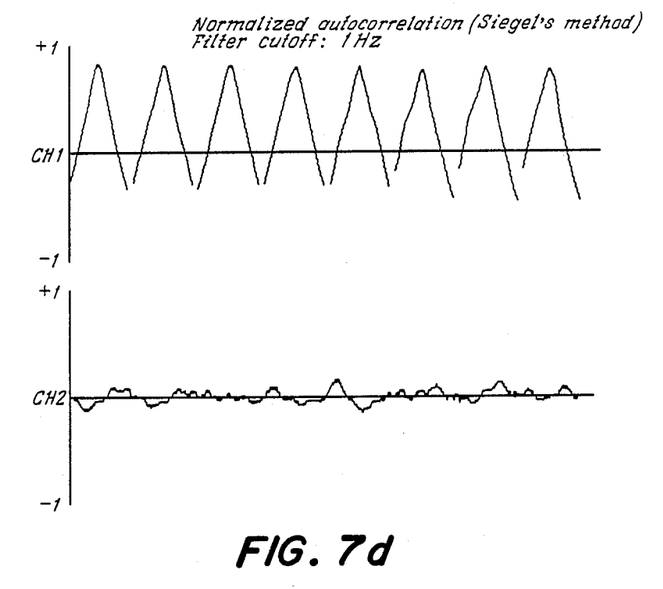
FIG. 7D is a complex autocorrelation of the filter signals.

Digital signal processing techniques can be divided into two types: time domain techniques and frequency domain techniques, both of which are well known in the art of signal processing. With frequency domain techniques, the digitized I and Q channel signals are transformed into the frequency domain, either with a Fast Fourier Transform (FFT) or some non Fourier spectral estimation algorithm, and a peak detection algorithm then estimates the frequency of the spectral line which corresponds to the cardiac rate. Time domain techniques require the processing of time domain signals with filtering and autocorrelation algorithms to obtain other time domain signals in which the time period between relative maxima can be more easily detected than in the original signal. Time domain techniques require less processing time to obtain an initial estimate of heart rate and, therefore, are preferred to frequency domain techniques. FIGS. 7A–D illustrate the process of heart rate termination. The I and Q channels from the output of the VSM are shown in FIG. 7A. These two signals are transformed into the frequency domain using a Fast Fourier Transform (FFT) algorithm. The resultant signals are depicted in FIG. 7B. FIG. 7C shows the I and Q channel signals after they are digitally high pass filtered. The cutoff frequency is 1 Hz. The complex autocorrelation of the filter signals is shown in FIG. 7D. The real part of the complex autocorrelation is used to calculate the rates displayed at the bottom of the figure. The digital filtering algorithm employed is the window technique. More complex filter design procedures can achieve better filters for a given filter length. More specifically, these more complex filter designs can yield filters with similar performance to the filters used to obtain the data in FIG. 7C, but the filter length could be reduced substantially, therefore decreasing computation time.

Comparison of FIGS. 7C and 7D reveals that the autocorrelation process yields a signal more suitable for a peak detection algorithm. The autocorrelation algorithm used is based on a method described by G. Hoshal, M. Siegel and R. Zapp in "A Microwave Heart Monitor and Life Detection System," published in 1984 in *IEEE Frontiers of Engineering and Computing in Health Care* on pp. 331-333. The method described by Hoshal et al. is incorporated by reference herein. Each of the eight autocorrelation segments shown in FIG. 7D was computed for lags between 60 and 120. Since the sampling frequency is 100 Hz, the sampling period is 10 milliseconds, and an autocorrelation lag of 60 corresponds to a time delay of 60 (10 ms)=0.6 seconds, or to a heart rate of 1.67 Hz or 100 beats per minute. Similarly, an autocorrelation lag of 120 corresponds to a heart rate of 50 beats per minute.

Four hundred samples of the filtered VSM output are used to compute each of the 8 autocorrelation segments. As a result, four seconds of data are required to compute each heart estimate shown in FIG. 7D. If the number of samples is too large, the aperiodic nature of the heart beat signal tends to flatten the autocorrelation. If the number of samples is too small, the record might not include an entire heart beat cycle. Each successive autocorrelation calculation starts at 100 points (corresponding to one second) further in the data record. The contrast between 7C and 7D clearly demonstrates the ability of the autocorrelation to enhance the presence of the heart beat signal.

While the invention has been described with respect to a preferred physical embodiment constructed in accordance therewith, the same is by way of example only and is not to be taken by way of limitation. It will be apparent to those skilled in the art that various modifications and improvements may be made without departing from the scope and spirit of the invention. For example, while specific frequencies or frequency ranges have been given for various components within the VSM 10 it will be evident to those skilled in the art that other embodiments can be developed employing different frequencies or frequency ranges. Thus, specific operating frequencies of the voltage controlled microwave oscillator 12, crystal oscillator 40 filters 56, 60, 72 are not limitations of the VSM 10. Similarly, the VSM is not limited by the type of ramp circuitry 36, weighting circuitry 52, liquid low pass filter 62, or synchronous detection circuitry 58 disclosed herein. Other digital sampling rates may also be used with the VSM 10. Furthermore, while the present system has been described as applicable for the non-contact measurement of heart rate and respiratory rate, it will be evident to those skilled in the art that the present system may be used to measure other types of potentially useful diagnostic information concerning cardiac and respiratory mechanical functions which can be derived from the VSM waveform by appropriate signal processing. Accordingly, it is to be understood that the invention is not limited by the specific illustrative embodiment, but only by the scope of the appended claims.

What is claimed is:

1. An apparatus for measuring simultaneously the heart and respiration rates of a subject comprising:
   transmitting means for directing a beam of frequency modulated, continuous wave radio frequency energy towards a body portion of said subject;
   receiving means for receiving said frequency modulated beam as a motion-related, phase modulated reflected signal from said body portion; and
   signal processing means for extracting the heart and respiration rates from said phase modulated reflected signal.

2. The apparatus of claim 1 wherein the transmitting means comprises:
   voltage controlled oscillator means to produce a continuous wave radio frequency signal output;
   modulator means for providing a time-varying ramp waveform to frequency modulate said continuous wave radio frequency signal output of said voltage controllable oscillator means;
   directional coupler means to split the oscillator's output into a first signal for transmission and a second signal for mixing with said phase modulated reflected signal;
   attenuator means to control the radiated power of said first signal output and said second signal output; and antenna means for transmitting said first signal output toward said body portion.

3. The apparatus of claim 2 wherein said modulator means comprises a digital timing circuit means for providing a first reference signal and a second reference signal, said reference signals having a relative phase difference of 90°.

4. The apparatus of claim 3 wherein said modulator means further comprises an analog ramp generator circuit means for forming the time-varying ramp waveform used to frequency modulate said radio frequency signal output of said voltage controllable oscillator means.

5. The apparatus of claim 3 wherein the receiving means comprises:
   antenna means for receiving said phase-modulated reflected signal from said subject;
   mixing means for combining said received phase-modulated reflected signal with said second signal output from said voltage controllable oscillator means to produce a different signal output containing harmonic frequency components of the time-varying ramp weigh form;
   preamplifier means for amplifying and filtering noise from the different signal output from said mixing means to produce a detected signal; and
   demodulator means for synchronously detecting in-phase and quadrature components from said detected signal.

6. The apparatus of claim 5 wherein the demodulator means comprises:
   a first bandpass filter means to remove said harmonic frequency components from said detected signal output from said preamplifier means and said first bandpass filter means providing a first detected output signal and a second detected output signal;
   a first synchronous detector having inputs comprising said first reference signal from said digital timing circuit means and said first detected output signal, and the output of said first synchronous detector comprising the in-phase component of said detected signal;
   a second synchronous detector having inputs comprising said second reference signal from said digital timing circuit means and said second detected output signal, and the output of said second synchronous detector comprising a quadrature component of said detected signal; and a plurality of second bandpass filters to filter the output of each of said synchronous detectors.

7. The apparatus of claim 6 wherein the demodulator means further comprises a weighting circuit to suppress range sidelobes in said detected signal by multiplying said detected signal by a weighting function to form a weighted detected signal.

8. The apparatus of claim 7 wherein the weighting function consists of a sinusoidal term and a DC offset term which describes the Hanning window.

9. The apparatus of claim 7 wherein the weighting function consists of a sinusoidal term and a DC offset term which describes the Hamming window.

10. The apparatus of claim 9 wherein the weighting circuit comprises an operational amplifier-based bi-quad lowpass filter having a first potentiometer connected to the input of said bi-quad low pass filter to vary the amplitude of the sinusoidal term in the weighting function, a second potentiometer connected to the input of said bi-quad low pass filter to generate a DC offset term, a summing junction connected to the input of said bi-quad low pass filter to add the sinusoidal term and the DC offset term, and a third potentiometer connected between the input and the output of said bi-quad low pass filter to set precisely the cutoff frequency of said bi-quad lowpass filter.

11. The apparatus of claim 6 wherein the signal processing means comprises:
 a plurality of sampling means for measuring the filtered outputs of each of said synchronous detectors at a specified rate and producing a plurality of digital sampled outputs;
 a plurality of digital filtering means for passing each of said plurality of digital sampled outputs above a cutoff frequency to produce a plurality of filtered digital sampled outputs; and
 algorithm means for computing the autocorrelation function of the plurality of said filtered digital sampled outputs.

12. The apparatus of claim 5 further comprising:
 a single antenna means for transmitting a beam of frequency modulated, continuous wave radio frequency energy and for receiving a phase modulated reflected signal;
 a circulator means for recovering said received phase modulated reflected signal from said antenna means; and
 isolator means to prevent leakage of said second signal output from said voltage controlled oscillator means from reaching said antenna means.

13. A method for measuring simultaneously the heart and respiration rates of a subject comprising the steps of:
 transmitting a beam of frequency modulated, continuous wave radio frequency energy towards a body portion of said subject;
 receiving said frequency modulated beam as a motion-related, phase modulated reflected signal from said body portion of said subject; and
 processing the phase modulated reflected signal to extract the heart and respiration rates from said phase modulated reflected signal.

14. The method claim 13 wherein the step of transmitting a beam of frequency modulated, continuous wave radio frequency energy comprises:
 producing a continuous wave radio frequency signal;
 modulating said continuous wave radio frequency signal with a time-varying ramp waveform to produce a frequency modulated, continuous wave radio frequency signal;
 splitting said frequency modulated, continuous wave radio frequency signal into a first signal for transmission and a second signal for mixing with said phase modulated reflected signal;
 controlling the radiated power of said first signal; and
 transmitting said first signal towards the body portion of said subject.

15. The method of claim 14 wherein the step of modulating further comprises generating a pair of reference signals having a relative phase difference of 90°.

16. The method of claim 15 wherein the step of receiving a motion-related, phase modulated reflected signal comprises:
 receiving said frequency modulated beam as phase-modulated reflected signal from said subject;
 mixing said phase-modulated reflected signal with said second signal to produce a difference signal output containing harmonics of said time-varying ramp waveform;
 amplifying and filtering said difference signal output to produce a detected signal;
 demodulating said detected signal to produce in-phase and quadrature components of said phase modulated reflected signal.

17. The method of claim 16 wherein the step of demodulating said detected signal comprises:
 filtering said detected signal to remove from said detected signal the harmonic frequency components;
 inverting said filtered detected signal to produce a first filtered signal and a second filtered signal, said first filtered signal and said second filtered signal being equal in amplitude but opposite in phase;
 mixing said first filtered signal with the first of said pair of said reference signals to form an in-phase output signal;
 mixing said second filtered signal with the second of said pair of reference signals to form a quadrature output signal,
 filtering the in-phase output signal to remove DC and high frequency mixing components to form a filtered in-phase signal; and
 filtering the quadrature output signal to remove DC and high frequency mixing components to form a filtered quadrature signal.

18. The method of claim 16 wherein the step of demodulating said detected signal includes multiplying said detected signal output by a weighting function to suppress range sidelobes contained in said detected signal.

19. The method of claim 18 wherein the step of processing the phase-modulated reflected signal to extract the heart rate and respiration rates comprises:
 sampling the filtered in-phase signal at a specified rate to produce a digital sampled in-phase output;
 sampling the filtered quadrature signal at a specified rate to produce a digital sampled quadrature output;
 high-pass filtering the digital sampled in-phase output to remove low frequency components;
 high-pass filtering the digital sampled quadrature output to remove low frequency components; and
 performing an autocorrelation on the high-pass filtered digital sampled in-phase output and the high-pass filtered digital sampled quadrature output.

20. An apparatus for measuring diagnostic information regarding the mechanical function of the heart, lungs, chest wall, or any anatomical part of the body of a subject undergoing motion comprising:

transmitting means for directing a beam of frequency modulated, continuous wave radio frequency energy towards a selected body portion of said subject;

receiving said frequency modulating beam as means for receiving a motion-related, phase modulated reflected signal from said selected body portion; and signal processing means for extracting the diagnostic information of interest from said motion-related phase modulated reflected signal.

21. A method for measuring diagnostic information regarding the mechanical function of the heart, lungs, chest wall, or any anatomical part of the body of a subject undergoing motion comprising:

transmitting a beam of frequency modulated, continuous wave radio frequency energy towards a selected body portion of said subject;

receiving said frequency modulated beam as a motion-related, phase modulated reflected signal from said selected body portion of said subject; and processing the phase modulated reflected signal to extract the diagnostic information of interest from said phase modulated reflected signal.

* * * * *